(12) United States Patent
Trivedi et al.

(10) Patent No.: US 12,405,187 B2
(45) Date of Patent: Sep. 2, 2025

(54) INSERTION APPARATUS FOR USE WITH ROTARY MACHINES

(71) Applicant: General Electric Company, Schenectady, NY (US)

(72) Inventors: Deepak Trivedi, Halfmoon, NY (US); Grover Andrew Bennett, Jr., Esperance, NY (US); Sandeep Kumar, Bengaluru (IN); Manoj Kumar Koyithitta Meethal, Bengaluru (IN); David Mulford Shaddock, Troy, NY (US); Andrew Crispin Graham, Badminton (GB); Stephen Paul Leclerc, Jr., Lake Luzerne, NY (US)

(73) Assignee: General Electric Company, Evendale, OH (US)

( * ) Notice: Subject to any disclaimer, the term of this patent is extended or adjusted under 35 U.S.C. 154(b) by 0 days.

(21) Appl. No.: 16/696,025

(22) Filed: Nov. 26, 2019

(65) Prior Publication Data

US 2021/0102870 A1    Apr. 8, 2021

(30) Foreign Application Priority Data

Oct. 4, 2019    (IN) .............................. 201941040204

(51) Int. Cl.
*G01M 15/14*    (2006.01)
*A61B 17/32*    (2006.01)
(Continued)

(52) U.S. Cl.
CPC ....... *G01M 15/14* (2013.01); *A61B 17/32002* (2013.01); *F01D 5/005* (2013.01);
(Continued)

(58) Field of Classification Search
CPC ........... G01M 15/14; A61B 17/320758; A61B 17/32002; F01D 25/00; F01D 25/285; F01D 5/005
See application file for complete search history.

(56) References Cited

U.S. PATENT DOCUMENTS

| | | |
|---|---|---|
| 338,310 A | 3/1886 | JM |
| 1,774,986 A | 9/1930 | MacKenzie |

(Continued)

FOREIGN PATENT DOCUMENTS

| | | |
|---|---|---|
| CA | 2960352 A1 | 9/2017 |
| CA | 3077622 A1 | 4/2019 |

(Continued)

OTHER PUBLICATIONS

FET20 (Wireless Borescope, Klein Tools, Jan. 2019) (Year: 2019).*
(Continued)

*Primary Examiner* — Kyle R Quigley
(74) *Attorney, Agent, or Firm* — Fitch, Even, Tabin & Flannery LLP

(57) ABSTRACT

An insertion apparatus for use with a rotary machine includes a body extending from an insertion end to a steering end and sized to fit within an annular cavity. The body has a first stiffness and curves along a circumference of the annular cavity as the insertion end travels through the annular cavity. The insertion apparatus also includes a stiffener coupled to the body and extending from the steering end to the insertion end. The stiffener has a second stiffness greater than the first stiffness. The insertion apparatus further includes at least one maintenance device coupled to the insertion end of the insertion apparatus and a displacement mechanism configured to adjust a position of the at least one maintenance device relative to the body.

19 Claims, 4 Drawing Sheets

(51) Int. Cl.
*F01D 5/00* (2006.01)
*F01D 25/00* (2006.01)
*F01D 25/28* (2006.01)
*A61B 17/3207* (2006.01)

(52) U.S. Cl.
CPC .......... *F01D 25/00* (2013.01); *F01D 25/285* (2013.01); *A61B 17/320758* (2013.01)

(56) References Cited

U.S. PATENT DOCUMENTS

| | | | |
|---|---|---|---|
| 1,987,972 | A | 1/1935 | Rhein |
| 2,073,903 | A | 3/1937 | O'Neil |
| 2,510,198 | A | 6/1950 | Tesmer |
| 2,974,676 | A | 3/1961 | Hagelthorn |
| 3,096,962 | A | 7/1963 | Johannes |
| 3,190,286 | A | 6/1965 | Stokes |
| 3,266,059 | A | 8/1966 | Stelle |
| 3,270,641 | A | 9/1966 | Gosselin |
| 3,583,393 | A | 6/1971 | Takahashi |
| 3,625,084 | A | 12/1971 | Siebert |
| 3,778,170 | A | 12/1973 | Howell |
| 4,035,137 | A | 7/1977 | Arand |
| 4,041,695 | A | 8/1977 | Harper |
| 4,095,418 | A | 6/1978 | Mansson |
| 4,170,489 | A | 10/1979 | Magnus |
| 4,215,979 | A | 8/1980 | Morishita |
| 4,227,584 | A | 10/1980 | Driver |
| 4,242,863 | A | 1/1981 | Bailey |
| 4,483,326 | A | 11/1984 | Yamaka |
| 4,625,936 | A | 12/1986 | Hadden, Sr. |
| 4,651,718 | A | 3/1987 | Collins |
| 4,655,673 | A | 4/1987 | Hawkes |
| 4,696,544 | A * | 9/1987 | Costella .......... G02B 23/26  600/102 |
| 4,703,888 | A | 11/1987 | Kawamura |
| 4,713,120 | A | 12/1987 | Hodgens, II |
| 4,714,339 | A | 12/1987 | Lau |
| 4,730,960 | A | 3/1988 | Lewis |
| 4,735,501 | A * | 4/1988 | Ginsburgh ......... G02B 23/2476  385/118 |
| 4,757,258 | A | 7/1988 | Kelly, Jr. |
| 4,773,395 | A | 9/1988 | Suzuki |
| 4,790,294 | A | 12/1988 | Allred, III |
| 4,790,624 | A | 12/1988 | Van Hoye |
| 4,826,087 | A | 5/1989 | Chinery |
| 4,846,573 | A | 7/1989 | Taylor |
| 4,890,602 | A | 1/1990 | Hake |
| 4,911,206 | A | 3/1990 | Gropp |
| 4,972,048 | A | 11/1990 | Martin |
| 4,991,565 | A | 2/1991 | Takahashi |
| 5,090,205 | A | 2/1992 | Foster |
| 5,102,221 | A | 4/1992 | Desgranges |
| 5,164,826 | A | 11/1992 | Dailey |
| 5,203,646 | A | 4/1993 | Landsberger |
| 5,254,809 | A | 10/1993 | Martin |
| 5,271,382 | A | 12/1993 | Chikama |
| 5,323,962 | A | 6/1994 | Jassby |
| 5,337,733 | A | 8/1994 | Bauerfeind |
| 5,339,845 | A | 8/1994 | Huddas |
| 5,372,162 | A | 12/1994 | Frey |
| 5,385,102 | A | 1/1995 | Villedieu |
| 5,390,402 | A | 2/1995 | White |
| 5,399,164 | A | 3/1995 | Snoke |
| 5,408,970 | A | 4/1995 | Burkhard |
| 5,482,029 | A | 1/1996 | Sekiguchi |
| 5,501,156 | A | 3/1996 | Richter |
| 5,558,665 | A | 9/1996 | Kieturakis |
| 5,644,394 | A | 7/1997 | Owens |
| 5,667,023 | A | 9/1997 | Harrell |
| 5,755,731 | A | 5/1998 | Grinberg |
| 5,787,897 | A | 8/1998 | Kieturakis |
| 5,807,241 | A | 9/1998 | Heimberger |
| 5,816,769 | A | 10/1998 | Bauer |
| 5,842,381 | A | 12/1998 | Feiten |
| 6,123,273 | A | 9/2000 | Loprinzo |
| 6,156,974 | A | 12/2000 | Blase |
| 6,213,974 | B1 | 4/2001 | Smith |
| 6,216,439 | B1 | 4/2001 | Nakamoto |
| 6,287,206 | B1 | 9/2001 | Stage |
| 6,311,704 | B1 | 11/2001 | Foster |
| 6,371,148 | B1 | 4/2002 | Tripp |
| 6,431,824 | B2 | 8/2002 | Schotsch |
| 6,432,046 | B1 * | 8/2002 | Yarush ............... A61B 1/07  600/179 |
| 6,478,033 | B1 | 11/2002 | Foster |
| 6,481,195 | B1 | 11/2002 | Blase |
| 6,542,230 | B1 | 4/2003 | Luke |
| 6,643,877 | B1 | 11/2003 | Amtenbrink |
| 6,698,456 | B2 | 3/2004 | Neubauer |
| 6,783,491 | B2 | 8/2004 | Saadat |
| 6,800,016 | B2 * | 10/2004 | Wittenberg ............. A63H 3/04  446/376 |
| 6,837,846 | B2 | 1/2005 | Jaffe |
| 6,941,974 | B2 | 9/2005 | Utaki |
| 6,943,570 | B2 | 9/2005 | Duffy |
| 6,955,023 | B2 | 10/2005 | Rotheroe |
| 6,957,781 | B2 | 10/2005 | Gowens |
| 6,974,411 | B2 | 12/2005 | Belson |
| 7,150,416 | B2 | 12/2006 | Martin |
| 7,171,279 | B2 | 1/2007 | Buckingham |
| 7,182,024 | B2 | 2/2007 | Pfeiffer |
| 7,182,025 | B2 | 2/2007 | Ghorbel |
| 7,185,407 | B2 | 3/2007 | Boyl-Davis |
| 7,258,521 | B2 | 8/2007 | Guerra |
| 7,509,735 | B2 | 3/2009 | Philip |
| 7,543,518 | B2 | 6/2009 | Buckingham |
| 7,559,340 | B2 | 7/2009 | Ikeda |
| 7,571,735 | B2 | 8/2009 | Wagner |
| 7,654,143 | B2 | 2/2010 | Roney |
| 7,662,091 | B2 | 2/2010 | Bagley |
| 7,677,181 | B2 | 3/2010 | Boyl-Davis |
| 7,703,272 | B2 | 4/2010 | Wagner |
| 7,707,704 | B2 | 5/2010 | Crocker |
| 7,712,301 | B1 | 5/2010 | Wagner |
| 7,718,894 | B2 | 5/2010 | Blase |
| 7,741,563 | B2 | 6/2010 | Harada |
| 7,849,878 | B2 | 12/2010 | Kohler |
| 7,854,109 | B2 | 12/2010 | Zubiate |
| 7,883,674 | B2 | 2/2011 | Huang |
| 8,069,747 | B2 | 12/2011 | Buckingham |
| 8,096,030 | B2 | 1/2012 | Graichen |
| 8,100,031 | B2 | 1/2012 | Zubiate |
| 8,125,755 | B2 | 2/2012 | Garcia |
| 8,152,934 | B2 | 4/2012 | Lee |
| 8,190,294 | B2 | 5/2012 | Sjoestrand |
| 8,205,522 | B2 | 6/2012 | Buckingham |
| 8,206,488 | B2 | 6/2012 | Mantkowski |
| 8,299,785 | B2 | 10/2012 | Bousquet |
| 8,303,243 | B2 | 11/2012 | Fish |
| 8,327,518 | B2 | 12/2012 | Koerner |
| 8,374,722 | B2 | 2/2013 | Buckingham |
| 8,377,232 | B2 | 2/2013 | Myers |
| 8,395,300 | B2 | 3/2013 | Aabloo |
| 8,400,501 | B2 | 3/2013 | Heyworth |
| 8,409,248 | B2 | 4/2013 | Ginn |
| 8,453,533 | B2 | 6/2013 | Ryland |
| 8,505,204 | B2 | 8/2013 | Reverchon |
| 8,571,711 | B2 | 10/2013 | Jacobsen |
| 8,635,849 | B2 | 1/2014 | Tassone |
| 8,640,531 | B2 | 2/2014 | Remillard |
| 8,674,222 | B2 | 3/2014 | Hsieh |
| 8,714,038 | B2 | 5/2014 | Moran |
| 8,758,232 | B2 | 6/2014 | Graham |
| 8,786,848 | B2 | 7/2014 | Hatcher |
| 8,833,826 | B2 | 9/2014 | Garcia |
| 8,893,749 | B2 | 11/2014 | Perry |
| 8,920,579 | B2 | 12/2014 | Liedtke |
| 8,945,096 | B2 | 2/2015 | Zubiate |
| 8,959,902 | B2 | 2/2015 | Olivier |
| 8,991,163 | B2 | 3/2015 | Olivier |
| 8,992,421 | B2 | 3/2015 | Stand |
| 8,998,567 | B2 | 4/2015 | Scipio |
| 9,016,159 | B2 | 4/2015 | Kell |

(56) References Cited

U.S. PATENT DOCUMENTS

| | | |
|---|---|---|
| 9,016,293 B2 | 4/2015 | Battaglioli |
| 9,028,618 B2 | 5/2015 | Battaglioli |
| 9,127,234 B2 | 9/2015 | Hughes |
| 9,149,929 B2 | 10/2015 | Motzer |
| 9,187,700 B2 | 11/2015 | Huang |
| 9,220,398 B2 | 12/2015 | Woodley |
| 9,263,866 B2 | 2/2016 | Shimizu |
| 9,272,425 B2 | 3/2016 | Garcia |
| 9,294,737 B2 | 3/2016 | Hatcher, Jr. |
| 9,300,926 B2 | 3/2016 | Kell |
| 9,329,377 B2 | 5/2016 | Kell |
| 9,389,150 B2 | 7/2016 | Kimpel, Jr. |
| 9,399,299 B2 | 7/2016 | Hermey |
| 9,403,244 B2 | 8/2016 | Rautenberg |
| 9,409,292 B2 | 8/2016 | Smith |
| 9,435,750 B2 | 9/2016 | Matsumoto |
| 9,458,735 B1 | 10/2016 | Diwinsky |
| 9,492,906 B2 | 11/2016 | Rösing |
| 9,505,125 B2 | 11/2016 | Zubiate |
| 9,549,663 B2 | 1/2017 | Larkin |
| 9,581,440 B2 | 2/2017 | Ruhge |
| 9,726,628 B2 | 8/2017 | Ruhge |
| 9,733,195 B2 | 8/2017 | Colletti |
| 9,778,141 B2 | 10/2017 | Bancalari |
| 9,788,141 B2 | 10/2017 | Bancalari |
| 9,857,002 B2 | 1/2018 | Ott |
| 9,902,024 B2 | 2/2018 | Ernst |
| 9,909,694 B2 | 3/2018 | Graham |
| 9,951,647 B2 | 4/2018 | Rawson |
| 10,060,569 B2 | 8/2018 | Sivacoe |
| 10,085,624 B2 | 10/2018 | Isoda |
| 10,197,473 B2 | 2/2019 | Diwinsky |
| 10,213,919 B2 | 2/2019 | Axinte |
| 10,238,457 B2 | 3/2019 | Herrell |
| 10,265,810 B2 | 4/2019 | Diwinsky |
| 10,428,993 B2 | 10/2019 | Whitefield |
| 10,470,831 B2 | 11/2019 | Cohen |
| 10,488,349 B2 | 11/2019 | Sibbach |
| 10,618,162 B2 | 4/2020 | Norton |
| 10,639,805 B2 | 5/2020 | Saraliev |
| 10,775,315 B2 | 9/2020 | Mekala |
| 10,884,232 B1 | 1/2021 | Trivedi |
| 10,926,403 B1 | 2/2021 | Asokan |
| 10,962,345 B2 | 3/2021 | Graham |
| 10,967,504 B2 | 4/2021 | Simaan |
| 11,371,437 B2 | 6/2022 | Hawke |
| 11,413,763 B2 | 8/2022 | Lee |
| 11,419,692 B2 | 8/2022 | Kim |
| 11,518,048 B2 | 12/2022 | Saraliev |
| 11,613,003 B2 | 3/2023 | Graham |
| 11,692,650 B2 | 7/2023 | Graham |
| 11,707,819 B2 | 7/2023 | Graham |
| 11,752,622 B2 | 9/2023 | Graham |
| 11,787,069 B2 | 10/2023 | Curle |
| 11,793,536 B2 | 10/2023 | Walen |
| 12,091,981 B2 | 9/2024 | Foxall |
| 12,194,620 B2 | 1/2025 | Graham |
| 2003/0089267 A1 | 5/2003 | Ghorbel |
| 2003/0171736 A1* | 9/2003 | Bon .................. A61M 25/0141 |
| | | 604/525 |
| 2003/0229420 A1 | 12/2003 | Buckingham |
| 2004/0059191 A1* | 3/2004 | Krupa ............... A61M 25/0136 |
| | | 600/146 |
| 2004/0138525 A1 | 7/2004 | Saadat |
| 2004/0186350 A1 | 9/2004 | Brenneman |
| 2004/0193016 A1* | 9/2004 | Root .................... A61B 1/0052 |
| | | 600/146 |
| 2004/0249367 A1 | 12/2004 | Saadat |
| 2004/0255422 A1 | 12/2004 | Reback |
| 2005/0075538 A1 | 4/2005 | Banik |
| 2005/0107667 A1 | 5/2005 | Danitz |
| 2005/0124856 A1* | 6/2005 | Fujikura ........... A61M 25/0662 |
| | | 600/156 |
| 2005/0148287 A1 | 7/2005 | Moeller |
| 2005/0203340 A1 | 9/2005 | Butler |
| 2005/0204489 A1 | 9/2005 | Velez |
| 2005/0273085 A1 | 12/2005 | Hinman |
| 2006/0073348 A1 | 4/2006 | Farmer |
| 2006/0074283 A1 | 4/2006 | Henderson |
| 2006/0074383 A1 | 4/2006 | Boulais |
| 2006/0131908 A1 | 6/2006 | Tadano |
| 2006/0156851 A1 | 7/2006 | Jacobsen |
| 2006/0170386 A1 | 8/2006 | Anhalt |
| 2006/0258265 A1* | 11/2006 | Moeller .................. B24B 19/14 |
| | | 451/6 |
| 2008/0066821 A1 | 3/2008 | Komiya |
| 2008/0149141 A1 | 6/2008 | Sales |
| 2008/0161971 A1 | 7/2008 | Buckingham |
| 2008/0199304 A1 | 8/2008 | Moran |
| 2008/0218728 A1 | 9/2008 | Kirschner |
| 2008/0250769 A1 | 10/2008 | Wagner |
| 2009/0084108 A1 | 4/2009 | Prociw |
| 2009/0084408 A1 | 4/2009 | Thiemann |
| 2009/0084411 A1 | 4/2009 | Woodcock |
| 2009/0086014 A1 | 4/2009 | Lea |
| 2009/0132085 A1 | 5/2009 | Sjostrand |
| 2009/0216245 A1 | 8/2009 | Viola |
| 2009/0216374 A1 | 8/2009 | Low |
| 2009/0255102 A1 | 10/2009 | McMasters |
| 2009/0255116 A1 | 10/2009 | McMasters |
| 2009/0256007 A1 | 10/2009 | McMasters |
| 2009/0320891 A1 | 12/2009 | Liedtke |
| 2010/0030377 A1 | 2/2010 | Unsworth |
| 2010/0037924 A1 | 2/2010 | Gebhardt |
| 2010/0108107 A1 | 5/2010 | Mantkowski |
| 2010/0108377 A1* | 5/2010 | Terada ................ B60R 16/0215 |
| | | 174/72 A |
| 2010/0116292 A1 | 5/2010 | Wagner |
| 2010/0147330 A1 | 6/2010 | Kohler |
| 2010/0160736 A1 | 6/2010 | Padget |
| 2010/0234988 A1 | 9/2010 | Buckingham |
| 2010/0256447 A1* | 10/2010 | Dubi .................. A61B 1/00135 |
| | | 600/115 |
| 2010/0275404 A1 | 11/2010 | Myers |
| 2011/0030381 A1 | 2/2011 | Sordyl |
| 2011/0112527 A1* | 5/2011 | Hamilton, Jr. ...... A61B 17/3468 |
| | | 606/41 |
| 2011/0152879 A1 | 6/2011 | Williams |
| 2011/0174108 A1 | 7/2011 | Graham |
| 2011/0295427 A1 | 12/2011 | Motzer |
| 2011/0303053 A1 | 12/2011 | Schneider |
| 2011/0313243 A1 | 12/2011 | Zubiate |
| 2012/0067158 A1 | 3/2012 | Kell |
| 2012/0125164 A1 | 5/2012 | Kozak |
| 2012/0167547 A1 | 7/2012 | Zhang |
| 2012/0184817 A1 | 7/2012 | Sugiyama |
| 2012/0197241 A1 | 8/2012 | Golden |
| 2012/0260497 A1 | 10/2012 | White |
| 2012/0279273 A1 | 11/2012 | Broda |
| 2012/0312103 A1* | 12/2012 | Hannott ............. G02B 23/2476 |
| | | 73/865.8 |
| 2013/0074879 A1 | 3/2013 | Battaglioli |
| 2013/0125753 A1 | 5/2013 | Ono |
| 2013/0192353 A1* | 8/2013 | Hatcher ............. G02B 23/2484 |
| | | 73/112.01 |
| 2013/0199040 A1 | 8/2013 | Dudeck |
| 2013/0226033 A1 | 8/2013 | Eskuri |
| 2013/0255410 A1 | 10/2013 | Lee |
| 2013/0335530 A1 | 12/2013 | Hatcher, Jr. |
| 2013/0340559 A1 | 12/2013 | Danitz |
| 2014/0005683 A1 | 1/2014 | Stand |
| 2014/0012288 A1 | 1/2014 | Darisse |
| 2014/0055596 A1 | 2/2014 | Hatcher, Jr. |
| 2014/0058364 A1 | 2/2014 | Donhowe |
| 2014/0069460 A1 | 3/2014 | Kell |
| 2014/0125791 A1 | 5/2014 | Arellano |
| 2014/0133269 A1* | 5/2014 | Hansen ............. A61B 1/00078 |
| | | 367/7 |
| 2014/0260755 A1 | 9/2014 | Dong |
| 2014/0371764 A1 | 12/2014 | Oyola |
| 2015/0032252 A1 | 1/2015 | Galluzzo |
| 2015/0036150 A1 | 2/2015 | Kobayashi |
| 2015/0064008 A1 | 3/2015 | Lewis |
| 2015/0159557 A1 | 6/2015 | Scipio |

(56) References Cited

U.S. PATENT DOCUMENTS

| | | |
|---|---|---|
| 2015/0202013 A1 | 7/2015 | Teichtmann |
| 2015/0233263 A1 | 8/2015 | Battaglioli |
| 2015/0246449 A1 | 9/2015 | Sakai |
| 2015/0300920 A1 | 10/2015 | Deascanis |
| 2015/0338353 A1 | 11/2015 | Bancalari |
| 2015/0341600 A1 | 11/2015 | Hatcher, Jr. |
| 2015/0360629 A1 | 12/2015 | Sekino |
| 2016/0000629 A1 | 1/2016 | Jackson |
| 2016/0008990 A1 | 1/2016 | Franz |
| 2016/0031078 A1 | 2/2016 | Kapoor |
| 2016/0032761 A1 | 2/2016 | Griffiths |
| 2016/0040803 A1 | 2/2016 | Steeger |
| 2016/0052129 A1 | 2/2016 | Ekas |
| 2016/0114488 A1 | 4/2016 | Mascorro Medina |
| 2016/0146036 A1 | 5/2016 | Richter |
| 2016/0174816 A1 | 6/2016 | Choset |
| 2016/0175057 A1 | 6/2016 | Ibach |
| 2016/0182776 A1 | 6/2016 | Huang |
| 2016/0186602 A1 | 6/2016 | Saenz |
| 2016/0339584 A1 | 11/2016 | Esteban Finck |
| 2017/0023154 A1 | 1/2017 | Jaeker |
| 2017/0095922 A1 | 4/2017 | Licht |
| 2017/0100197 A1 | 4/2017 | Zubiate |
| 2017/0120457 A1 | 5/2017 | Saraliev |
| 2017/0129110 A1 | 5/2017 | Ohm |
| 2017/0157719 A1 | 6/2017 | Diwinsky |
| 2017/0167289 A1 | 6/2017 | Diwinsky |
| 2017/0167953 A1 | 6/2017 | Diwinsky |
| 2017/0175569 A1 | 6/2017 | Rawson |
| 2017/0191376 A1 | 7/2017 | Eriksen |
| 2017/0219814 A1 | 8/2017 | Letter |
| 2017/0219815 A1 | 8/2017 | Letter |
| 2017/0239762 A1 | 8/2017 | Roberts |
| 2017/0274484 A1 | 9/2017 | Roberts |
| 2017/0319048 A1 | 11/2017 | Ikeda |
| 2017/0328497 A1 | 11/2017 | Dantin |
| 2017/0359530 A1 | 12/2017 | Boudin |
| 2017/0361470 A1 | 12/2017 | Otero Del Real |
| 2018/0058233 A1 | 3/2018 | Norton |
| 2018/0071039 A1* | 3/2018 | Barnett ............... A61B 34/70 |
| 2018/0094538 A1 | 4/2018 | Tibbetts |
| 2018/0119568 A1 | 5/2018 | Negoescu |
| 2018/0149038 A1 | 5/2018 | Eriksen |
| 2018/0156062 A1 | 6/2018 | Dede |
| 2018/0156132 A1 | 6/2018 | Dede |
| 2018/0214220 A1 | 8/2018 | Kan |
| 2018/0231162 A1 | 8/2018 | Zeng |
| 2018/0242958 A1 | 8/2018 | Dayton |
| 2018/0313225 A1 | 11/2018 | Millhaem |
| 2018/0361960 A1 | 12/2018 | Yamamoto |
| 2019/0022877 A1 | 1/2019 | Akin |
| 2019/0046010 A1 | 2/2019 | Tojo |
| 2019/0054638 A1 | 2/2019 | Norton |
| 2019/0145498 A1 | 5/2019 | Yoon |
| 2019/0190190 A1 | 6/2019 | Bourgeas |
| 2019/0246878 A1 | 8/2019 | Bodner |
| 2019/0277770 A1 | 9/2019 | Mekala |
| 2019/0292938 A1 | 9/2019 | Wang |
| 2019/0308319 A1 | 10/2019 | Walters |
| 2019/0358813 A1 | 11/2019 | Graham |
| 2019/0358833 A1 | 11/2019 | Graham |
| 2019/0360794 A1 | 11/2019 | Graham |
| 2019/0366536 A1 | 12/2019 | Graham |
| 2019/0383158 A1 | 12/2019 | Diwinsky |
| 2019/0383161 A1 | 12/2019 | Graham |
| 2020/0113412 A1 | 4/2020 | Jensen |
| 2020/0114497 A1 | 4/2020 | Graham |
| 2020/0114505 A1 | 4/2020 | Kikuchi |
| 2020/0114528 A1 | 4/2020 | Graham |
| 2020/0182345 A1 | 6/2020 | Gu |
| 2020/0205908 A1 | 7/2020 | Julian |
| 2020/0224552 A1 | 7/2020 | Millhaem |
| 2020/0316789 A1 | 10/2020 | Sohmshetty |
| 2020/0319119 A1* | 10/2020 | Peters ............... F01D 21/003 |
| 2020/0323599 A1 | 10/2020 | Kim |
| 2020/0359879 A1 | 11/2020 | Cahill |
| 2020/0405142 A1* | 12/2020 | Whitaker ............... A61B 1/317 |
| 2021/0078165 A1 | 3/2021 | Tang |
| 2021/0137354 A1 | 5/2021 | Bob |
| 2021/0223142 A1* | 7/2021 | Sasaki ............... G01M 15/14 |
| 2021/0229269 A1 | 7/2021 | Graham |
| 2021/0229270 A1 | 7/2021 | Graham |
| 2021/0231239 A1 | 7/2021 | Graham |
| 2021/0285374 A1 | 9/2021 | Hawke |
| 2021/0388737 A1 | 12/2021 | Foxall |
| 2022/0221706 A1 | 7/2022 | Trivedi |
| 2022/0221707 A1 | 7/2022 | Trivedi |
| 2022/0290608 A1 | 9/2022 | Hawke |
| 2022/0314430 A1 | 10/2022 | Graham |
| 2023/0194234 A1 | 6/2023 | Graham |
| 2024/0011413 A1 | 1/2024 | Millheam |
| 2024/0280033 A1 | 8/2024 | Foxall |
| 2024/0326266 A1 | 10/2024 | Graham |
| 2025/0163824 A1 | 5/2025 | Diwinsky |

FOREIGN PATENT DOCUMENTS

| | | |
|---|---|---|
| CA | 3043720 A1 | 11/2019 |
| CN | 86101283 A | 8/1986 |
| CN | 1162516 | 10/1997 |
| CN | 1050781 C | 3/2000 |
| CN | 1656312 | 8/2005 |
| CN | 1678937 | 10/2005 |
| CN | 1903517 | 1/2007 |
| CN | 101048101 | 10/2007 |
| CN | 101048102 | 10/2007 |
| CN | 101528111 A | 9/2009 |
| CN | 101881218 | 11/2010 |
| CN | 201769177 | 3/2011 |
| CN | 201800016 | 4/2011 |
| CN | 102257292 | 11/2011 |
| CN | 102292013 A | 12/2011 |
| CN | 102687057 | 9/2012 |
| CN | 102711585 | 10/2012 |
| CN | 102729240 A | 10/2012 |
| CN | 102871636 | 1/2013 |
| CN | 203370761 U | 1/2014 |
| CN | 103895012 A | 7/2014 |
| CN | 104175325 | 12/2014 |
| CN | 104582909 A | 4/2015 |
| CN | 103639156 B | 7/2015 |
| CN | 104870141 | 8/2015 |
| CN | 105144514 | 12/2015 |
| CN | 105377116 | 3/2016 |
| CN | 105431106 | 3/2016 |
| CN | 105436127 A | 3/2016 |
| CN | 105927820 | 9/2016 |
| CN | 106113019 | 11/2016 |
| CN | 106163431 | 11/2016 |
| CN | 106166746 | 11/2016 |
| CN | 106427289 A | 2/2017 |
| CN | 106659438 | 5/2017 |
| CN | 106988798 | 7/2017 |
| CN | 107205622 | 9/2017 |
| CN | 107468339 A | 12/2017 |
| CN | 108356747 | 8/2018 |
| CN | 108472025 | 8/2018 |
| CN | 207941781 | 10/2018 |
| CN | 108890656 | 11/2018 |
| CN | 108972527 | 12/2018 |
| CN | 109068938 | 12/2018 |
| CN | 109476019 | 3/2019 |
| CN | 109561935 | 4/2019 |
| CN | 109716194 | 5/2019 |
| CN | 110001286 | 7/2019 |
| CN | 110462169 | 11/2019 |
| CN | 110529254 | 12/2019 |
| CN | 110757412 | 2/2020 |
| CN | 111037602 | 4/2020 |
| CN | 111486008 | 8/2020 |
| CN | 113146599 | 7/2021 |
| CN | 113232042 | 8/2021 |
| DE | 3504824 | 8/1986 |
| DE | 4102211 | 8/1991 |

(56) References Cited

FOREIGN PATENT DOCUMENTS

| | | | |
|---|---|---|---|
| DE | 4102211 A1 * | 8/1991 | |
| DE | 29902753 U | 6/1999 | |
| DE | 10160922 | 5/2003 | |
| DE | 102019002892 A1 | 10/2020 | |
| DE | 102020106508 | 9/2021 | |
| EP | 1216797 | 6/2002 | |
| EP | 1216797 A1 | 6/2002 | |
| EP | 1489269 A2 | 12/2004 | |
| EP | 1574675 A2 | 9/2005 | |
| EP | 2011619 A2 | 1/2009 | |
| EP | 1914010 A3 | 9/2010 | |
| EP | 2237931 A1 | 10/2010 | |
| EP | 2267508 | 12/2010 | |
| EP | 22677508 A2 | 12/2010 | |
| EP | 1967295 B1 | 1/2011 | |
| EP | 2320262 | 5/2011 | |
| EP | 2052792 A3 | 6/2011 | |
| EP | 2353739 A1 | 8/2011 | |
| EP | 2375104 | 10/2011 | |
| EP | 2286933 B1 | 11/2011 | |
| EP | 2275648 B1 | 3/2012 | |
| EP | 1903188 B1 | 5/2013 | |
| EP | 2597273 A2 | 5/2013 | |
| EP | 2629655 | 8/2013 | |
| EP | 3061923 A1 | 8/2016 | |
| EP | 3072642 A2 | 9/2016 | |
| EP | 1908928 B1 | 12/2016 | |
| EP | 3153604 A1 | 4/2017 | |
| EP | 3176365 A1 | 6/2017 | |
| EP | 3572632 | 11/2019 | |
| EP | 3572632 A1 | 11/2019 | |
| EP | 3879075 | 9/2021 | |
| FR | 2956608 A1 | 8/2011 | |
| FR | 2995996 A1 | 3/2014 | |
| FR | 3082136 A1 | 12/2019 | |
| GB | 779248 | 7/1957 | |
| GB | 1437405 A | 5/1976 | |
| GB | 2199842 | 7/1988 | |
| GB | 2228644 A | 8/1990 | |
| JP | H10146316 A | 6/1998 | |
| JP | 2006184832 A | 7/2006 | |
| JP | 2013510339 A | 3/2013 | |
| MX | 2010013223 A1 * | 12/2010 | ............ B63B 35/03 |
| NO | 162227 B | 8/1989 | |
| TW | 201341090 | 10/2013 | |
| WO | 9116598 A1 | 10/1991 | |
| WO | 0006336 A1 | 2/2000 | |
| WO | 2009081164 A1 | 7/2009 | |
| WO | 2011092891 | 8/2011 | |
| WO | 2012042921 A1 | 4/2012 | |
| WO | 2012054829 | 4/2012 | |
| WO | 2012054829 A2 | 4/2012 | |
| WO | 2016063074 A2 | 4/2016 | |
| WO | 2017037723 | 3/2017 | |
| WO | 2017221982 A1 | 12/2017 | |
| WO | 2018001967 A1 | 1/2018 | |
| WO | 2019076876 | 4/2019 | |
| WO | 2019076876 A1 | 4/2019 | |
| WO | 2019097688 | 5/2019 | |
| WO | 2021040376 | 3/2021 | |
| WO | 2021040376 A1 | 3/2021 | |

OTHER PUBLICATIONS

DE4102211A1 English Translation (Year: 1991).*
Mascarenas, et al., A compliant mechanism for inspecting extremely confined spaces, Smart Materials and Structures, Oct. 26, 2017, vol. 26, pp. 1-16.
Huang et al., In-Situ Continuous Coke Deposit Removal by Catalytic Steam Gasification for Fuel-Cooled Thermal Management, Journal of Engineering for Gas Turbines and Power, vol. 134, Oct. 2012, 8 Pages.
Mascarenas et al., "A Compliant Mechanism for Inspecting Extremely Confined Spaces" Smart Materials and Structures, vol. No. 26, pp. 1-16, Oct. 26, 2017.
U.S. Appl. No. 16/577,331; Notice of Allowance and Fees Due (PTOL-85) mailed Jul. 25, 2022; (pp. 1-5).
U.S. Appl. No. 16/735,191; Non-Final Rejection mailed Aug. 3, 2022; (pp. 1-11).
U.S. Appl. No. 16/750,665; Non-Final Rejection mailed Jul. 20, 2022; (pp. 1-9).
U.S. Appl. No. 16/751,802; Final Rejection mailed Jul. 28, 2022; (pp. 1-9).
Wickham et al., High Heat Flux Surface Coke Deposition and Removal Assessment, Technical Paper, Air Force Research Laboratory, Edwards AFB, Jan. 2015, California, 21 Pages.
U.S. Appl. No. 17/144,487; Non-Final Rejection mailed Aug. 23, 2022; (pp. 1-6).
U.S. Appl. No. 16/751,802; Supplemental Notice of Allowance mailed Feb. 27, 2023; (pp. 1-4).
U.S. Appl. No. 16/898,629; Final Rejection mailed Feb. 28, 2023; (pp. 1-22).
U.S. Appl. No. 16/696,025, filed Nov. 26, 2019.
U.S. Appl. No. 16/750,665, filed Jan. 23, 2020.
U.S. Appl. No. 16/750,743, filed Jan. 23, 2020.
U.S. Appl. No. 16/751,802, filed Jan. 24, 2020.
U.S. Appl. No. 16/813,829, filed Mar. 10, 2020.
U.S. Appl. No. 16/898,629, filed Jun. 11, 2020.
U.S. Appl. No. 17/144,487, filed Jan. 8, 2021.
U.S. Appl. No. 15/986,958, filed May 23, 2018.
US Final Office Action from U.S. Appl. No. 15/986,958 dated Sep. 9, 2020, 10 pgs.
US Non-Final Office Action from U.S. Appl. No. 15/986,958 dated Apr. 23, 2020, 12 pgs.
US Notice of Allowance and Notice of Allowability, dated Nov. 18, 2020, from U.S. Appl. No. 15/986,958, 9 pgs.
U.S. Appl. No. 16/751,802; Non-Final Rejection mailed Feb. 28, 2022; (pp. 1-12).
U.S. Appl. No. 16/750,743; Non-Final Rejection mailed Apr. 27, 2022; (pp. 1-12).
U.S. Appl. No. 16/577,331; Non-Final Rejection mailed Jan. 19, 2022; (pp. 1-8).
U.S. Appl. No. 16/577,331; Notice of Allowance and Fees Due (PTOL-85) mailed Nov. 7, 2022; (pp. 1-5).
U.S. Appl. No. 16/577,331; Notice of Allowance and Fees Due (PTOL-85) mailed Nov. 7, 2022; (pp. 1-16).
U.S. Appl. No. 16/750,665; Notice of Allowance and Fees Due (PTOL-85) mailed Nov. 17, 2022; (pp. 1-5).
U.S. Appl. No. 16/750,743; Final Rejection mailed Nov. 7, 2022; (pp. 1-13).
U.S. Appl. No. 16/750,743; Final Rejection mailed Nov. 7, 2022; (pp. 1-28).
U.S. Appl. No. 16/751,802; Notice of Allowance and Fees Due (PTOL-85) mailed Oct. 19, 2022; (pp. 1-7).
U.S. Appl. No. 16/898,629; Non-Final Rejection mailed Sep. 13, 2022; (pp. 1-14).
U.S. Appl. No. 17/219,577; Notice of Allowance and Fees Due (PTOL-85) mailed Jan. 4, 2023; (pp. 1-5).
U.S. Appl. No. 17/144,487; Final Rejection mailed Jan. 11, 2023; (pp. 1-5).
U.S. Appl. No. 16/577,268; Non-Final Rejection mailed Jan. 20, 2023; (pp. 1-29).
U.S. Appl. No. 16/750,743; Notice of Allowance and Fees Due (PTOL-85) mailed Jan. 23, 2023; (pp. 1-5).
U.S. Appl. No. 17/824,691; Notice of Allowance and Fees Due (PTOL-85) mailed Jun. 21, 2023; (pp. 1-9).
U.S. Appl. No. 16/577,331; Notice of Allowance and Fees Due (PTOL-85) mailed May 26, 2023; (pp. 1-5).
U.S. Appl. No. 16/735,191; Notice of Allowance and Fees Due (PTOL-85) mailed Mar. 27, 2023; (pp. 1-5).
U.S. Appl. No. 16/750,665; Notice of Allowance and Fees Due (PTOL-85) mailed Mar. 24, 2023; (pp. 1-6).
U.S. Appl. No. 16/750,743; Notice of Allowance and Fees Due (PTOL-85) mailed May 16, 2023; (pp. 1-5).

(56) References Cited

OTHER PUBLICATIONS

U.S. Appl. No. 16/898,629; Non-Final Rejection mailed Jun. 7, 2023; (pp. 1-14).
U.S. Appl. No. 17/144,487; Non-Final Rejection mailed Mar. 22, 2023; (pp. 1-6).
U.S. Appl. No. 16/898,629; Final Office Action mailed Oct. 10, 2023; (pp. 1-12).
U.S. Appl. No. 17/824,691; Notice of Allowance and Fees Due (PTOL-85) mailed Oct. 10, 2023; (pp. 1-8).
U.S. Appl. No. 15/812,004, filed Nov. 14, 2017.
U.S. Appl. No. 15/914,469, filed Mar. 7, 2018.
U.S. Appl. No. 16/008,475; Final Rejection mailed Mar. 2, 2023; (pp. 1-21).
U.S. Appl. No. 16/008,475; Final Rejection mailed Aug. 4, 2022; (pp. 1-8).
U.S. Appl. No. 16/008,475; Final Rejection mailed Dec. 15, 2023; (pp. 1-24).
U.S. Appl. No. 16/008,475; Non-Final Rejection mailed Jun. 15, 2023; (pp. 1-23).
U.S. Appl. No. 16/008,475; Non-Final Rejection mailed Oct. 21, 2022; (pp. 1-18).
U.S. Appl. No. 17/144,487; Non-Final Rejection mailed Apr. 18, 2024; (pp. 1-12).
U.S. Appl. No. 16/008,475; Non-Final Rejection mailed Apr. 22, 2024; (pp. 1-33).
U.S. Appl. No. 16/577,268; Notice of Allowance and Fees Due (PTOL-85) mailed Feb. 26, 2024; (pp. 1-12).
U.S. Appl. No. 16/898,629; Notice of Allowance and Fees Due (PTOL-85) mailed Jan. 17, 2024; (pp. 1-7).
U.S. Appl. No. 17/144,435; Non-Final Rejection mailed Mar. 11, 2024; (pp. 1-12).
U.S. Appl. No. 17/144,487; Final Rejection mailed Feb. 12, 2024; (pp. 1-5).
U.S. Appl. No. 17/552,848; Requirement for Restriction/Election mailed Feb. 26, 2024; (pp. 1-8).
U.S. Appl. No. 18/328,076; Non-Final Rejection mailed Feb. 27, 2024; (pp. 1-14).
Bakhshi, M. et al., Tunnel Segmental Lining Geometry, Tolerance and Measurement, Tunnelling & Trenchless Conference, 2018, 10 pp.
U.S. Appl. No. 16/577,268; Non-Final Rejection mailed Jun. 10, 2024; (pp. 1-28).
U.S. Appl. No. 17/552,848; Non-Final Rejection mailed Jun. 21, 2024; (pp. 1-38).
U.S. Appl. No. 17/552,848; Final Rejection mailed Oct. 28, 2024; (pp. 1-23).
U.S. Appl. No. 16/577,268; Notice of Allowance and Fees Due (PTOL-85) mailed Nov. 20, 2024; (pp. 1-15).
U.S. Appl. No. 18/328,076; Notice of Allowance and Fees Due (PTOL-85) mailed Dec. 13, 2024; (pp. 1-8).
U.S. Appl. No. 18/328,076; Notice of Allowance and Fees Due (PTOL-85) mailed Dec. 26, 2024; (pp. 1-5).
U.S. Appl. No. 16/008,475; Final Rejection mailed Nov. 4, 2024; (pp. 1-50).
U.S. Appl. No. 16/898,629; Notice of Allowance and Fees Due (PTOL-85) mailed Aug. 2, 2024; (pp. 1-5).
U.S. Appl. No. 18/733,557; Application filed Jun. 4, 2024, entitled "Selectively Flexible Extension Tool".
U.S. Appl. No. 16/577,268; Notice of Allowance mailed Sep. 13, 2024; (pp. 1-16).
U.S. Appl. No. 17/144,487; Final Rejection mailed Sep. 18, 2024; (pp. 1-14).
U.S. Appl. No. 16/577,268; Notice of Allowance and Fees Due (PTOL-85) mailed Sep. 13, 2024; (pp. 1-15).
U.S. Appl. No. 18/328,076; Final Rejection mailed Sep. 24, 2024; (pp. 1-12).
U.S. Appl. No. 17/144,435; Final Rejection mailed Jan. 24, 2025; (pp. 1-12).
U.S. Appl. No. 17/144,487; Final Rejection mailed Jan. 23, 2025; (pp. 1-18).
U.S. Appl. No. 18/328,076; Notice of Allowance and Fees Due (PTOL-85) mailed Jan. 14, 2025; (pp. 1-5).
U.S. Appl. No. 18/328,076; Notice of Allowance and Fees Due (PTOL-85) mailed Feb. 25, 2025; (pp. 1-5).
U.S. Appl. No. 17/144,435; Notice of Allowance mailed Apr. 23, 2025; (pp. 1-7).
U.S. Appl. No. 17/144,435; Notice of Allowance and Fees Due (PTOL-85) mailed Apr. 23, 2025; (pp. 1-7).
U.S. Appl. No. 17/144,487; Notice of Allowance and Fees Due (PTOL-85) mailed Apr. 30, 2025; (pp. 1-24).

* cited by examiner

INSERTION APPARATUS FOR USE WITH ROTARY MACHINES

CROSS REFERENCE TO RELATED APPLICATIONS

This application claims priority to Indian Patent Application Serial No. 201941040204 filed Oct. 4, 2019, entitled INSERTION APPARATUS FOR USE WITH ROTARY MACHINES, which is hereby incorporated by reference in its entirety.

BACKGROUND

The field of the disclosure relates generally to an insertion apparatus and, more particularly, to an insertion apparatus for use with rotary machines having annular cavities.

At least some known rotary machines, such as turbines for aircraft engines and gas and steam powered turbines for industrial applications, include an outer case and at least one rotor that carries multiple stages of rotating airfoils, i.e., blades, which rotate with respect to the outer case. In addition, the outer case carries multiple stages of stationary airfoils, i.e., guide vanes. The blades and guide vanes are arranged in alternating stages. In at least some known rotary machines, shrouds are disposed on the radially inner surfaces of a stator to form a ring seal around tips of the blades.

At least some rotary machines are inspected periodically to determine if components of the rotary machines need repair and/or replacement. However, some components of the rotary machine may be difficult to access and inspect without disassembly of the rotary machine. For example, some components, such as clips attaching the shrouds to shroud hangers, are positioned in annular cavities extending circumferentially around the shrouds. However, the size, shape, and location of the annular cavities prevent at least some known inspection apparatus from accessing and inspecting the clips. Moreover, the annular cavities may be obstructed by components, such as the clips, that extend at least partially into the annular cavities.

Accordingly, it is desirable to provide an insertion apparatus for use with a rotary machine that is configured to inspect components positioned along an annular cavity of the rotary machine.

BRIEF DESCRIPTION

In one aspect, an insertion apparatus for use with a rotary machine is provided. The rotary machine defines an annular cavity extending along a circumference. The insertion apparatus includes an insertion end positionable within the annular cavity and configured to travel through the annular cavity. The insertion apparatus also includes a steering end opposite the insertion end. The insertion apparatus further includes a body extending from the insertion end to the steering end and sized to fit within the annular cavity. The body has a first stiffness and curves along the circumference as the insertion end travels through the annular cavity. The insertion apparatus also includes a stiffener coupled to the body and extending from the steering end to the insertion end. The stiffener has a second stiffness greater than the first stiffness. The insertion apparatus further includes at least one maintenance device coupled to the insertion end of the insertion apparatus and a displacement mechanism configured to adjust a position of the at least one maintenance device relative to the body.

In another aspect, a system for use with a rotary machine is provided. The rotary machine defines an annular cavity extending along a circumference. The system includes an insertion apparatus including a body extending from an insertion end to a steering end. The body is sized to fit within the annular cavity and is curves along the circumference. The system also includes at least one maintenance device coupled to the insertion end of the insertion apparatus and a displacement mechanism configured to adjust a position of the at least one maintenance device relative to the body. The system further includes a guide tube positionable in a port of the rotary machine and configured to define a path for the insertion apparatus into the annular cavity. The guide tube is curved to form an at least partially helical path around objects and is sized to extend adjacent an opening into the annular cavity.

In yet another aspect, a method of inspecting a rotary machine is provided. The rotary machine defines an annular cavity extending along a circumference. The method includes positioning a guide tube in a port of the rotary machine to define a path for an insertion apparatus into the annular cavity. The guide tube is curved to form an at least partially helical shape. The method also includes positioning the insertion apparatus along the path and into the annular cavity. The insertion apparatus includes a body having an insertion end and a steering end opposite the insertion end. The body is sized to fit within the annular cavity and is curves along the circumference. The method further includes directing the insertion end of the insertion apparatus through the annular cavity. At least one maintenance device is coupled to the insertion end of the insertion apparatus. The method also includes positioning the at least one maintenance device adjacent a portion of the rotary machine using a displacement mechanism configured to adjust a position of the at least one maintenance device relative to the body.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of this disclosure. These features are believed to be applicable in a wide variety of systems comprising one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Embodiments described herein provide a system for use with a rotary machine having an annular cavity. The system includes an insertion apparatus configured to position a maintenance device along the annular cavity of the rotary machine. In addition, in some embodiments, the system includes a guide tube positionable in a port of the rotary machine and configured to guide the insertion apparatus into the annular cavity. For example, the guide tube is curved and has a helical shape. During deployment, the insertion apparatus is inserted along a path defined by the guide tube into the annular cavity and directed along the annular cavity. The insertion apparatus is sized and shaped to fit within and move along the annular cavity. The maintenance device is coupled to an insertion end of the insertion apparatus and is positionable relative to the rotary machine using a displacement mechanism. As a result, the system allows inspection and/or repair of components at locations within the annular cavity of the rotary machine.

Figure 1:
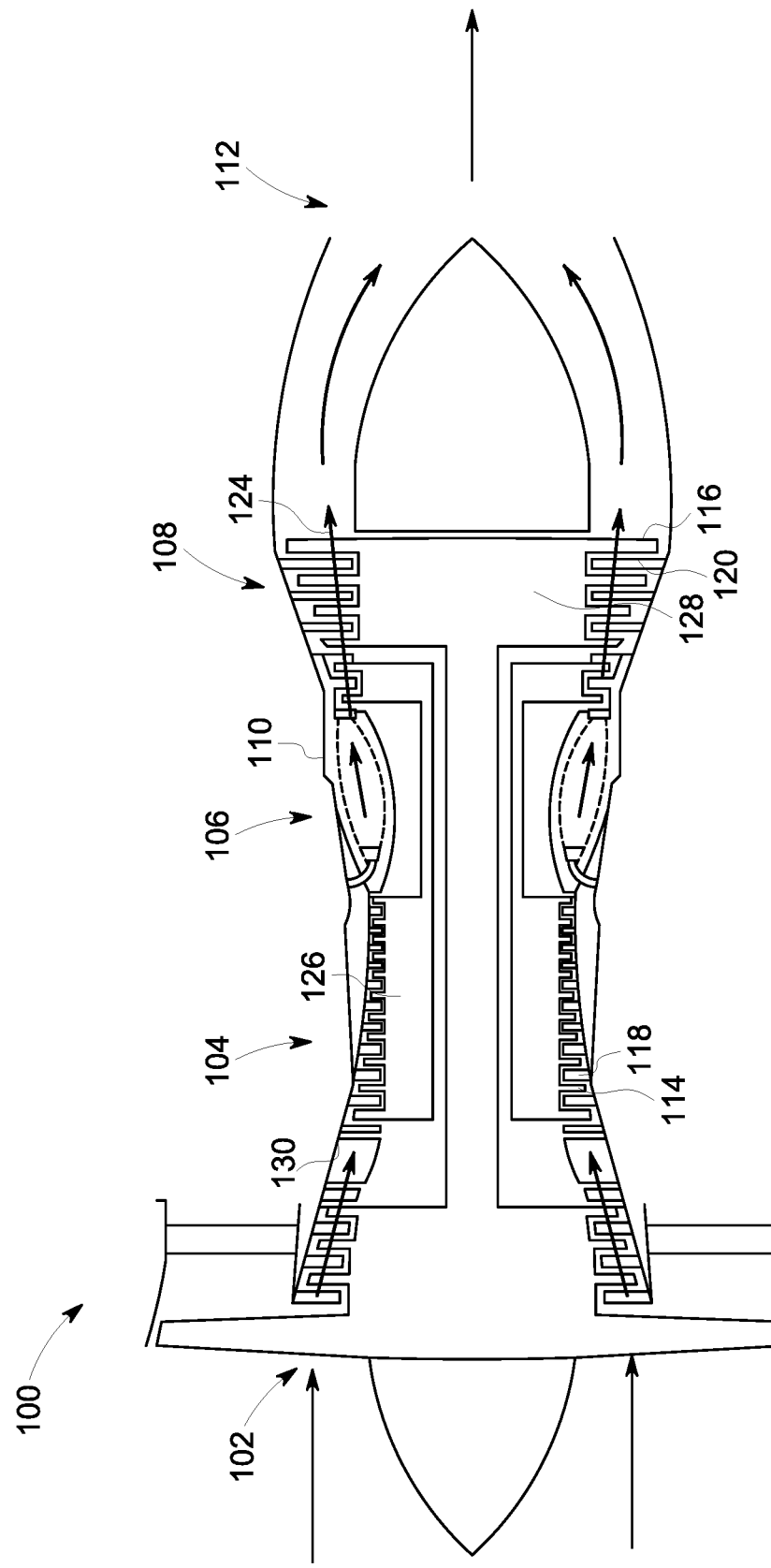
FIG. 1 is a cross-sectional schematic view of an exemplary rotary machine.

FIG. 1 is a cross-sectional schematic view of an exemplary rotary machine. In the exemplary embodiment, the rotary machine includes a turbine assembly 100. In alternative embodiments, the rotary machine includes any assembly. For example, in some embodiments, the rotary machine includes, without limitation, any of the following: a compressor, a blower, a pump, a turbine, a motor, and a generator.

In the exemplary embodiment, turbine assembly 100 includes an inlet 102, a compressor 104, a combustor 106, a turbine 108, an outer case 110, and an exhaust 112. Fluid flows from inlet 102, through compressor 104, through combustor 106, through turbine 108 and is discharged through exhaust 112. Also, in the exemplary embodiment, compressor 104 and turbine 108 include airfoils configured to direct fluid through turbine assembly 100. In particular, compressor 104 and turbine 108 include blades 114, 116 and guide vanes 118, 120. Together, blades 114, 116, guide vanes 118, 120, and shrouds 122 (shown in FIG. 2) define a primary flowpath 124 of turbine assembly 100. This flowpath, combined with a flowpath through combustor 106, defines a primary cavity within turbine assembly 100. In alternative embodiments, turbine assembly 100 is configured in any manner that enables turbine assembly 100 to operate as described herein.

Blades 114, 116 are operably coupled with rotating shafts 126, 128 such that blades 114, 116 rotate when rotating shafts 126, 128 rotate. Accordingly, blades 114, 116 and rotating shafts 126, 128 form a rotor of turbine assembly 100. Guide vanes 118, 120 and shrouds 122 are stationary components and are coupled to an interior surface 130 of outer case 110. Blades 114, 116 and guide vanes 118, 120 are generally positioned alternatingly along the rotor axis within turbine assembly 100. In alternative embodiments, compressor 104 and/or turbine 108 includes any airfoils that enable turbine assembly 100 to operate as described herein.

Figure 2:
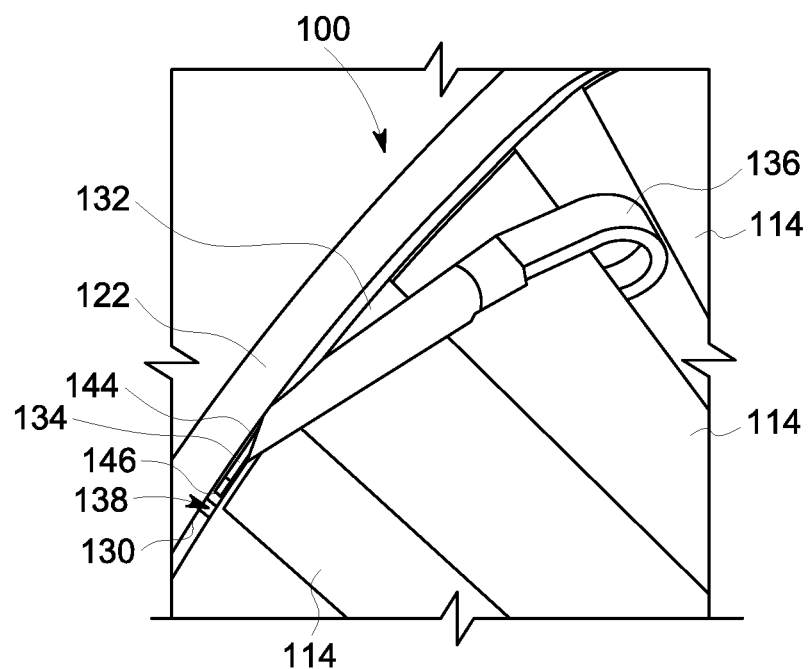
FIG. 2 is a schematic view of a system including an insertion apparatus and a guide tube positioned within a primary cavity of the rotary machine shown in FIG. 1.
Figure 3:
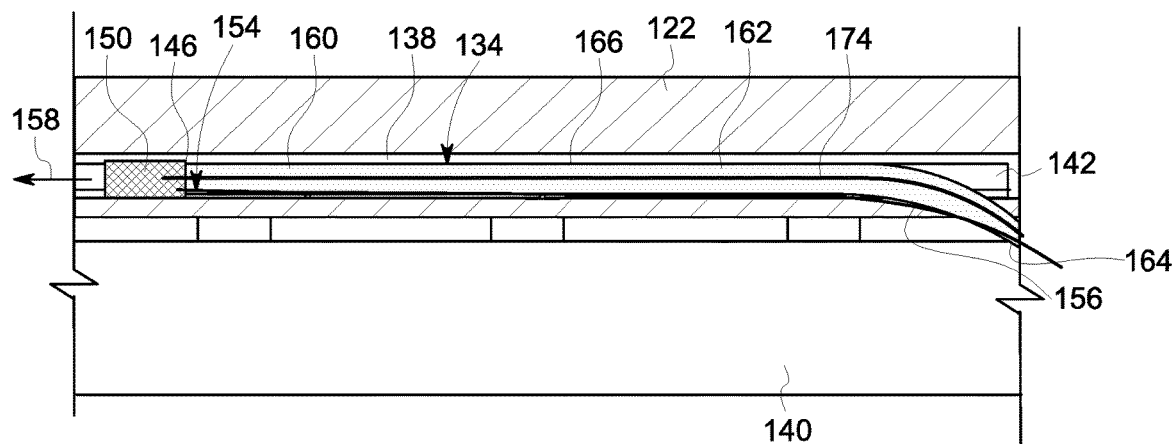
FIG. 3 is a schematic view of the insertion apparatus shown in FIG. 2 traveling along the annular cavity of the rotary machine shown in FIG. 1.

FIG. 2 is a schematic view of a system 132 including an insertion apparatus 134 and a guide tube 136 positioned in the primary cavity of turbine assembly 100. FIG. 3 is a schematic view of insertion apparatus 134 traveling along an annular cavity 138 of turbine assembly 100. Annular cavity 138 extends along a circumference of a respective shroud 122 of turbine assembly 100.

In the exemplary embodiment, shrouds 122 are at least partially supported by a hanger and extend circumferentially around blades 114, 116 and alongside a turbine central frame 140. Clips 142 couple shrouds 122 to hangers and secure shrouds 122 in position during operation of turbine assembly 100. In the exemplary embodiment, clips 142 are C-shaped and extend at least partially into annular cavity 138. Clips 142 are spaced apart along the circumference of each shroud 122. Accordingly, clips 142 are difficult to access from the exterior of turbine assembly 100 or from the primary cavity of turbine assembly 100. Insertion apparatus 134 is sized and shaped to fit within annular cavity 138 and facilitates inspection and/or repair at locations within annular cavity 138 that are difficult to access from an exterior of turbine assembly 100 by conventional means, such as using a borescope tool. Specifically, in contrast to at least some known insertion apparatus, insertion apparatus 134 is configured to extend into annular cavity 138 to facilitate inspection of clips 142.

During operation, insertion apparatus 134 enters turbine assembly 100 through any suitable access port or opening of turbine assembly 100. For example, in some embodiments, insertion apparatus 134 enters and/or exits turbine assembly 100 through any of inlet 102 (shown in FIG. 1), exhaust 112 (shown in FIG. 1), and/or an access port, such as an igniter, borescope, or fuel nozzle port. In the exemplary embodiment, insertion apparatus 134 is sized and shaped to fit within turbine assembly 100 and to travel along annular cavity 138. For example, insertion apparatus 134 has a height, length, and width that are less than a clearance required to fit within annular cavity 138. In alternative embodiments, insertion apparatus 134 is any size and shape that enables insertion apparatus 134 to operate as described herein.

Also, in the exemplary embodiment, guide tube 136 extends through a port of turbine assembly 100 and defines a path for insertion apparatus 134. For example, guide tube 136 defines an interior space sized to receive insertion apparatus 134 and allow insertion apparatus 134 to travel through guide tube 136. Guide tube 136 may be fixed to turbine assembly 100 by a flange (not shown) coupled to a port of turbine assembly 100. For example, in some embodiments, a flange extends around guide tube 136 and is sized to fit onto a port of turbine assembly 100. In alternative embodiments, guide tube 136 is coupled to turbine assembly 100 in any manner that enables guide tube 136 to operate as described herein.

In addition, in the exemplary embodiment, guide tube 136 is configured to direct insertion apparatus 134 into annular cavity 138 of turbine assembly 100. For example, guide tube 136 is curved and defines a curved path for insertion apparatus 134. Specifically, guide tube 136 is curved in three-dimensions and has a helical shape. Accordingly, guide tube 136 is able to guide insertion apparatus 134 around obstacles in the primary cavity of turbine assembly 100. In addition, guide tube 136 is sized such that a tip 144 of guide tube 136 is positioned proximate a target area within turbine assembly 100, e.g., an opening into annular cavity 138. In alternative embodiments, guide tube 136 is any size and shape that enables guide tube 136 to operate as described herein.

During operation, insertion apparatus 134 is used to inspect and/or repair any interior components of turbine assembly 100. For example, in some embodiments, insertion apparatus 134 is positioned adjacent a portion of interior surface 130 of turbine assembly 100 within annular cavity 138. Interior surface 130 may include a surface of clips 142. In some embodiments, insertion apparatus 134 detects a characteristic of interior surface 130. For example, in some embodiments, insertion apparatus 134 is used to generate an image of interior surface 130 and the image is examined to determine the condition of turbine assembly 100 and assess whether repairs are necessary. In further embodiments, insertion apparatus 134 includes a sensor that detects characteristics of interior surface 130. If repairs are necessary, in some embodiments, insertion apparatus 134 is used to repair interior surface 130. After inspection and/or repair of interior surface 130, insertion apparatus 134 exits turbine assembly 100 through any suitable access port or opening of turbine assembly 100, such as via the route of entry.

Figure 4:
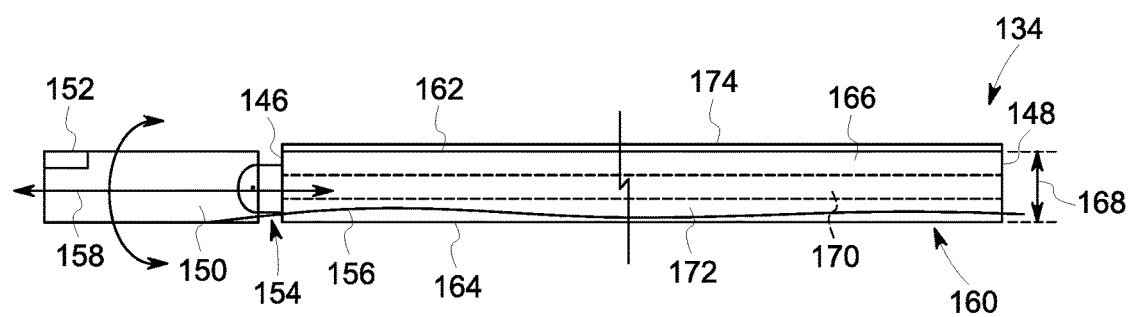
FIG. 4 is a side view of a portion of the insertion apparatus shown in FIGS. 2 and 3.

FIG. 4 is a side view of a portion of insertion apparatus 134. Insertion apparatus 134 includes an insertion end 146 and a steering end 148 opposite insertion end 146. Insertion end 146 is positionable within annular cavity 138 (shown in FIG. 3) of turbine assembly 100 (shown in FIG. 1) at target locations, such as adjacent clips 142 (shown in FIG. 3). In some embodiments, insertion end 146 is shaped to facilitate movement of insertion apparatus 134 through annular cavity 138 (shown in FIG. 3) without insertion apparatus 134 being caught on objects. For example, in some embodiments, insertion end 146 is curved. In further embodiments, insertion end 146 is angled, e.g., insertion end 146 has a V-shape.

Also, in the exemplary embodiment, insertion apparatus 134 includes at least one maintenance device 150 coupled to insertion end 146 of insertion apparatus 134 to allow insertion apparatus 134 to perform an inspection and/or repair operation within annular cavity 138 (shown in FIG. 3) of turbine assembly 100 (shown in FIG. 1). In some embodiments, maintenance device 150 includes at least one sensor 152 that is configured to contact surfaces. For example, in some embodiments, sensor 152 is an eddy current sensor. In alternative embodiments, insertion apparatus 134 includes any maintenance device 150 that enables insertion apparatus 134 to operate as described herein. For example, in some embodiments, maintenance device 150 of insertion apparatus 134 includes, without limitation, any of the following: an applicator, a drill, a grinder, a heater, a welding electrode, a sprayer, an optical sensor (e.g., visible, infrared, and/or multi-spectral sensor), a mechanical sensor (e.g., stylus profilometer, coordinate measurement probe, load transducer, linear variable differential transformer), a thermal sensor (e.g., pyrometer, thermocouple, resistance temperature detector), a magnetic sensor, an acoustic sensor (e.g., piezoelectric, microphone, ultrasound), and an electromagnetic sensor (e.g., eddy current, potential drop, x-ray).

In addition, in the exemplary embodiment, maintenance device 150 is positionable in a plurality of orientations using a displacement mechanism 154. For example, in the exemplary embodiment, maintenance device 150 is pivotably coupled to insertion end 146 of insertion apparatus 134. Displacement mechanism 154 includes a cable 156 extending from maintenance device 150 to steering end 148. Maintenance device 150 is selectively pivoted by manipulating cable 156. For example, maintenance device 150 is positionable between a first orientation in which maintenance device 150 is aligned with a translation direction 158 of insertion apparatus 134 and a second orientation in which insertion apparatus 134 extends at an angle relative to translation direction 158. The ability to position maintenance device 150 in a plurality of orientations facilitates precise positioning of maintenance device 150 relative to a target location. In alternative embodiments, maintenance device 150 is positionable in any manner that enables insertion apparatus 134 to operate as described herein.

Also, in the exemplary embodiment, insertion apparatus 134 includes a body 160 extending from insertion end 146 to steering end 148. Body 160 is sized and shaped to fit within annular cavity 138 (shown in FIG. 3). For example, body 160 includes a first surface 162, a second surface 164 opposite first surface 162, and edges 166 extending along first surface 162 and second surface 164. First surface 162 and second surface 164 extend from steering end 148 to insertion end 146 and define a thickness 168 of body 160 therebetween. Thickness 168 is less than a width of each of first surface 162 and second surface 164. For example, in some embodiment, thickness 168 of body 160 is less than about 0.02 inches. In addition, first surface 162 and second surface 164 are substantially smooth, e.g., free of bumps, perforations, folds, or other surface features. Accordingly, body 160 is ribbon-shaped. In alternative embodiments, body 160 has any shape that enables insertion apparatus 134 to function as described herein.

Moreover, in the exemplary embodiment, body 160 is flexible and conforms to a curve of annular cavity 138. Specifically, body 160 has a first stiffness and is configured to curve in a direction perpendicular to first surface 162 and second surface 164 along the curve of annular cavity 138. Accordingly, insertion apparatus 134 is able to travel within annular cavity 138 circumferentially along shroud 122 (shown in FIG. 2). Also, body 160 has a length that is greater than a circumference of shroud 122 such that insertion apparatus 134 is configured to extend from the exterior of turbine assembly 100 (shown in FIG. 2), into annular cavity 138 (shown in FIG. 2) and through the entirety of annular cavity 138. In the exemplary embodiment, body 160 includes at least one conductor 170, e.g., a flexible metal wire, encased within insulation 172. In alternative embodiments, insertion apparatus 134 includes any body 160 that enables insertion apparatus 134 to operate as described herein.

In addition, in the exemplary embodiment, insertion apparatus 134 includes a stiffener 174 coupled to and extending along body 160 from steering end 148 to insertion end 146. In some embodiments, stiffener 174 is coupled to body 160 or formed integrally with body 160. Stiffener 174 is configured to resist bending of body 160 and facilitate translation and steering of insertion apparatus 134 within annular cavity 138 (shown in FIG. 3). Moreover, stiffener 174 prevents body 160 from folding as insertion apparatus 134 is moved. Stiffener 174 has a second stiffness greater than the first stiffness of body 160. For example, in some embodiments, stiffener 174 includes a material that has a greater stiffness per unit volume than the material of body 160. In further embodiments, stiffener 174 has a thickness greater than thickness 168 of body 160. In the exemplary embodiment, stiffener 174 includes at least one cable and/or at least one hollow tube extending from steering end 148 to insertion end 146. Stiffener 174 has a width that is less than a width of body 160 and allows some flexing of body 160. In alternative embodiments, insertion apparatus 134 includes any stiffener 174 that enables insertion apparatus 134 to operate as described herein. In further embodiments, stiffener 174 is omitted.

In some embodiments, body 160 and/or stiffener 174 is configured to convey power and communication signals for maintenance device 150. In further embodiments, maintenance device 150 transmits and receives signals and/or power using any wired and/or wireless connections. For example, in some embodiments, a component, such as a harness or tether, extends from maintenance device 150 to the exterior of turbine assembly 100 and provides power to maintenance device 150, allows maintenance device 150 to send and/or receive signals, and/or transmits mechanical force, fluids, or thermal energy to maintenance device 150.

Figure 5:
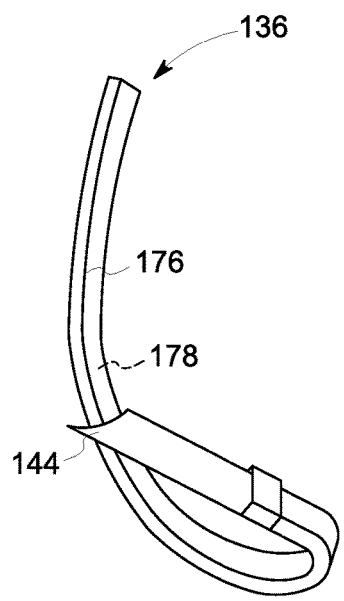
FIG. 5 is a perspective view of the guide tube shown in FIG. 2.

FIG. 5 is a perspective view of guide tube 136. Guide tube 136 includes a body 176 and tip 144. Together body 176 and tip 144 define an interior cavity 178 sized to receive insertion apparatus 134 (shown in FIG. 4). Guide tube 136 is configured to guide insertion apparatus 134 (shown in FIG. 2) toward annular cavity 138 (shown in FIG. 2). Body 176 is substantially rigid relative to insertion apparatus 134 (shown in FIG. 2) such that body 176 does not deform when insertion apparatus 134 travels through guide tube 136. In addition, body 176 is curved in 3-dimensions and forms a helical shape. When positioned in a port of turbine assembly 100 (shown in FIG. 2), guide tube 136 defines a path for insertion apparatus 134 around components of turbine assembly 100, such as blades 114 (shown in FIG. 2), and into annular cavity 138 (shown in FIG. 2). In alternative embodiments, guide tube 136 includes any body 176 that enables guide tube 136 to function as described herein. For example, in some embodiments, body 176 is segmented and the segments of body 176 are positionable relative to each other.

Also, in the exemplary embodiment, tip 144 is pliable and has a stiffness less than the stiffness of body 176. In addition, tip (144) is relatively flexible compared to the rest of guide tube 136. Accordingly, tip 144 may deform when contacted by insertion apparatus 134. Tip 144 facilitates guiding insertion apparatus 134 into the opening of annular cavity 138 when guide tube 136 is positioned proximate annular cavity 138. In alternative embodiments, guide tube 136 includes any tip that enables guide tube 136 to function as described herein.

Figure 6:
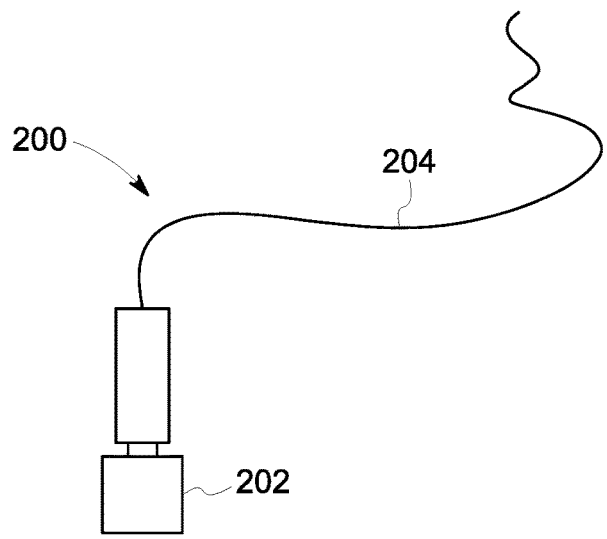
FIG. 6 is a perspective view of an alternative embodiment of a displacement mechanism for use with the insertion apparatus shown in FIGS. 2-4.

FIG. 6 is a perspective view of an alternative embodiment of a displacement mechanism 200 for use with the insertion apparatus 134 (shown in FIGS. 2-4). Displacement mechanism 200 is configured to adjust the orientation of maintenance device 150 (shown in FIG. 4) relative to insertion end 146 (shown in FIG. 4) of insertion apparatus 134. For example, displacement mechanism 200 includes an inflatable bladder 202 and a flexible tube 204 configured to deliver a fluid to inflatable bladder 202. Inflatable bladder 202 is configured to couple to maintenance device 150 (shown in FIG. 4). In addition, inflatable bladder 202 is configured to switch between a deflated position and an at least partially inflated position to adjust the position of maintenance device 150 relative to body 160 (shown in FIG. 4) of insertion apparatus 134 (shown in FIG. 4).

Also, in the exemplary embodiment, flexible tube 204 extends from insertion end 146 (shown in FIG. 4) to steering end 148 (shown in FIG. 4) and is configured to carry fluid such as air, water, and/or any other suitable fluid to inflatable bladder 202. In some embodiments, displacement mechanism 200 includes a valve or other regulatory mechanism to allow control of the fluid flow through flexible tube 204. In some embodiments, flexible tube 204 provides stiffness to body 160 (shown in FIG. 4) and acts as stiffener 174 (shown in FIG. 4) of insertion apparatus 134 (shown in FIG. 4).

Figure 7:
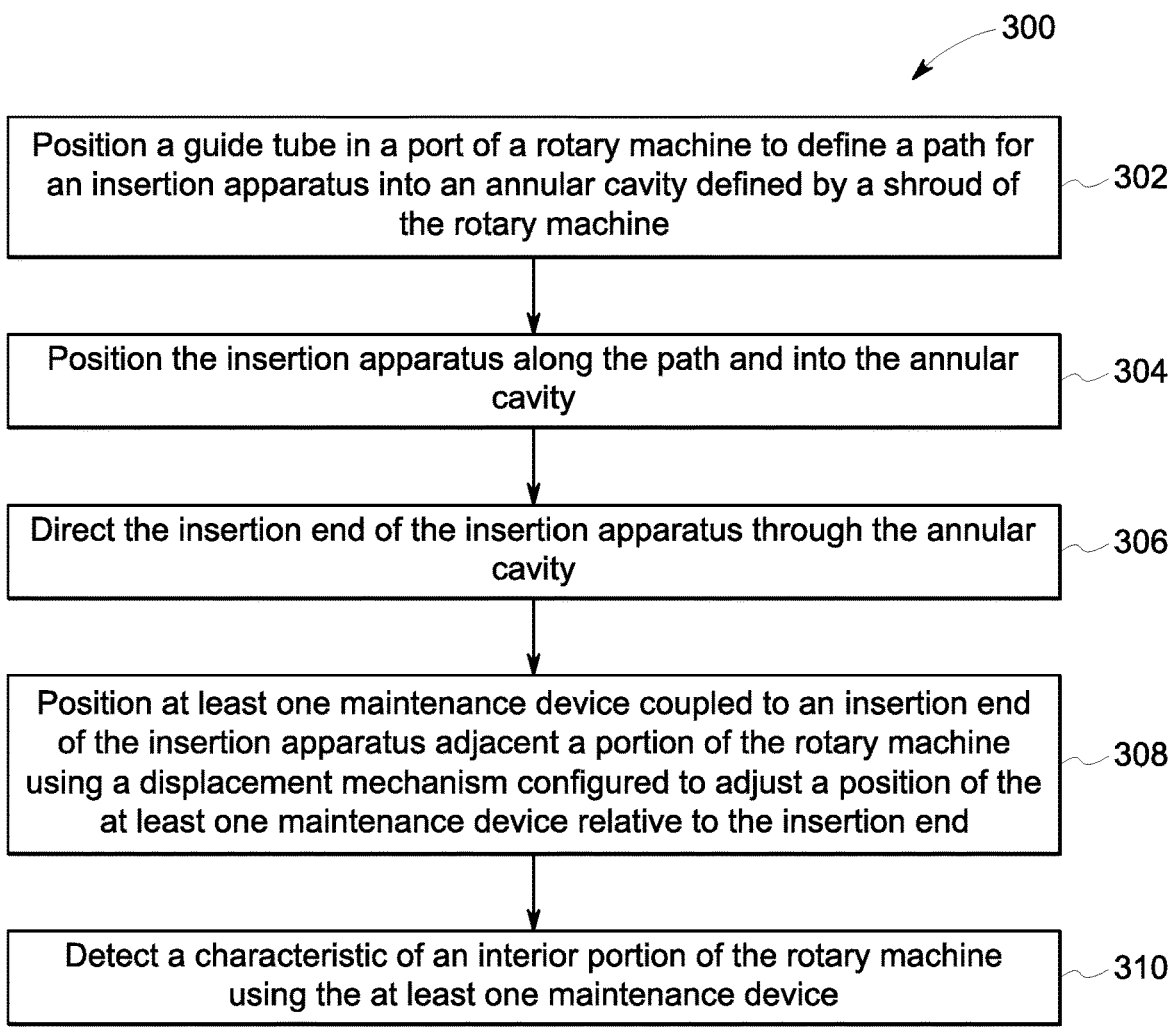
FIG. 7 is a flow chart of an exemplary method of inspecting a rotary machine.

FIG. 7 is a flow chart of an exemplary method 300 of inspecting turbine assembly 100 (shown in FIG. 1). In reference to FIGS. 1-3 and 7, method 300 includes positioning 302 guide tube 136 in a port of the rotary machine to define a path for insertion apparatus 134 into annular cavity 138 defined by shroud 122. For example, in some embodiments, a flange fits onto a port of turbine assembly 100 and couples guide tube 136 to turbine assembly 100. Guide tube 136 defines a path from an exterior of turbine assembly 100, through the port, and into annular cavity 138. Guide tube 136 is shaped to curve around obstacles within turbine assembly 100 and is sized such that tip 144 of guide tube 136 is positioned adjacent an opening into annular cavity 138. In alternative embodiments, guide tube 136 defines any path that enables system 132 to operate as described herein.

In addition, method 300 includes positioning 304 insertion apparatus 134 along the path and into annular cavity 138. For example, in some embodiments, insertion apparatus 134 is inserted into the interior cavity 178 of guide tube 136 and moved through guide tube 136. Guide tube 136 guides insertion apparatus 134 around obstacles within turbine assembly 100 and into annular cavity 138 as insertion apparatus 134 is moved along the path defined by guide tube 136. In some embodiments, method 300 includes deforming tip 144 to guide insertion apparatus 134 into annular cavity 138. For example, in some embodiments, tip 144 has a stiffness less than the stiffness of body 176 and allows insertion apparatus 134 to transition smoothly from guide tube 136 and into annular cavity 138.

Also, method 300 includes directing 306 insertion end 146 of insertion apparatus 134 through annular cavity 138. For example, in some embodiments, insertion end 146 of insertion apparatus 134 is directed through annular cavity 138 using a steering interface located at steering end 148. In some embodiments, insertion end 146 is directed by moving body 160 along translation direction 158. Insertion end 146 moves along the circumference of shroud 122 within annular cavity 138 as body 160 is moved in translation direction 158. After insertion end 146 has traveled around substantially the entire circumference of shroud 122 or has passed a desired target location, insertion apparatus 134 may be moved backwards along translation direction 158 within annular cavity 138. In alternative embodiments, insertion apparatus 134 is moved in any manner that enables insertion apparatus 134 to operate as described herein.

Also, method 300 includes positioning 308 maintenance device 150 coupled to insertion end 146 of insertion apparatus 134 adjacent a portion of the rotary machine using displacement mechanism 154. For example, in some embodiments, cable 156 of displacement mechanism 154 is used to pivot maintenance device 150 about insertion end 146 of insertion apparatus 134 such that maintenance device 150 contacts interior surface 130 of clips 142. In further embodiments, inflatable bladder 202 (shown in FIG. 6) is inflated/deflated to adjust the position of maintenance device 150.

Moreover, method 300 includes detecting 310 a characteristic of an interior portion of the rotary machine using maintenance device 150. For example, in some embodiments, maintenance device 150 includes sensor 152 with electrodes that contact clips 142 within annular cavity 138 to determine a characteristic of clips 142. Displacement mechanism 154 facilitates maintenance device 150 properly contacting clips 142 or other components of turbine assembly 100. Accordingly, insertion apparatus 134 is able to provide accurate and reliable information for components along annular cavity 138.

The above described embodiments provide a system for use with a rotary machine having an annular cavity. The system includes an insertion apparatus configured to position a maintenance device along the annular cavity of the rotary machine. In addition, in some embodiments, the system includes a guide tube positionable in a port of the rotary machine and configured to guide the insertion apparatus into the annular cavity. For example, the guide tube is curved and has a helical shape. During deployment, the insertion apparatus is inserted along a path defined by the guide tube into the annular cavity and directed along the annular cavity. The insertion apparatus is sized and shaped to fit within and move along the annular cavity. The maintenance device is coupled to an insertion end of the insertion apparatus and is positionable relative to the rotary machine using a displacement mechanism. As a result, the system allows inspection and/or repair of components at locations within the annular cavity of the rotary machine.

An exemplary technical effect of the methods, systems, and apparatus described herein includes at least one of: (a) reducing the time to inspect and/or repair a rotary device or other applicable circular mechanism; (b) increasing the accessibility of difficult-to-reach locations within a turbine assembly for inspection and/or in situ repair; (c) reducing the time that circular mechanisms are out of service for maintenance; (d) increasing the precision and/or reliability of inspection and repair of circular mechanisms; (e) reducing unplanned service outages for a circular mechanisms; (f) enhancing data capture for use in quantifying and/or modeling the service condition of at least some components of the circular mechanism; and (g) providing a system and method for inspecting shroud hanger clips within an annular cavity.

Exemplary embodiments of methods and systems for use with rotary machines are not limited to the specific embodiments described herein, but rather, components of systems and/or steps of the methods may be utilized independently and separately from other components and/or steps described herein. For example, the methods and systems may also be used in combination with other systems requiring inspection and/or repair of components, and are not limited to practice with only the systems and methods as described herein. Rather, the exemplary embodiment can be implemented and utilized in connection with many other applications, equipment, and systems that may benefit from using a service apparatus for inspection and/or repair.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An insertion apparatus for use with a rotary machine, the rotary machine defining an annular cavity extending along a circumference, said insertion apparatus comprising:
    an insertion end positionable within the annular cavity and configured to travel through the annular cavity;
    a steering end opposite said insertion end;
    a body extending from said insertion end to said steering end and sized to fit within the annular cavity, wherein said body includes a first material having a first material stiffness and curves along the circumference as said insertion end travels through the annular cavity;
    a stiffener integrally formed and fixed with respect to said body and extending from said steering end to said insertion end, wherein said stiffener includes a second material having a second material stiffness that is greater than the first material stiffness and is configured to resist bending of said body;
    wherein the stiffener is fixed adjacent to one edge of the body;
    wherein the edge of the body corresponding to the location of the stiffener leads an opposite edge of the body that does not correspond to the stiffener during insertion into the annular cavity;
    wherein the stiffener is configured to resist bending and prevent the body from folding when being translated into the annular cavity;
    wherein the body and stiffener comprise a uniform and uninterrupted cross-section extending from the insertion end to the steering end;
    wherein (1) arrangement of the stiffener fixed and adjacent to one edge of the body and (2) integral formation of the body with the stiffener are cooperatively effective to provide the body with an overall stiffness, the overall stiffness being constant and unchanged prior to deformation of the body and after deformation of the body as the body curves along the circumference during insertion and movement of the body through the annular cavity;
    wherein the stiffener is uncontrolled during insertion and movement of the body through the annular cavity;
    at least one maintenance device coupled to said insertion end of said insertion apparatus;
    a displacement mechanism configured to adjust a position of said at least one maintenance device relative to said body;
    a guide tube having a segmented body including segments that are positionable relative to each other, the body and stiffener axially movable through the segments of the guide tube; and
    wherein the guide tube is curved to form an at least partially helical shape.

2. The insertion apparatus in accordance with claim 1, wherein said body comprises a first surface and a second surface opposite said first surface, said first surface and said second surface extending from said steering end to said insertion end, said body having a thickness defined between said first surface and said second surface, wherein the thickness is less than a width of said first surface and said second surface, and wherein said body is configured to curve in a direction perpendicular to said first surface and said second surface.

3. The insertion apparatus in accordance with claim 1, wherein said at least one maintenance device is pivotably coupled to said insertion end, and wherein said displacement mechanism is configured to pivot said at least one maintenance device about said insertion end.

4. The insertion apparatus in accordance with claim 1, wherein said body is configured to convey power and communication signals for said at least one maintenance device.

5. The insertion apparatus in accordance with claim 1, wherein said at least one maintenance device comprises at least one of the following: an optical sensor, a mechanical sensor, a thermal sensor, a magnetic sensor, an acoustic sensor, and an electromagnetic sensor.

6. The insertion apparatus in accordance with claim 1, wherein the stiffener has a stiffener thickness greater than a thickness of the body.

7. The insertion apparatus in accordance with claim 1, wherein the body is a ribbon-shaped body.

8. The insertion apparatus in accordance with claim 7, wherein the body has a thickness less than about 0.02 inches.

9. The insertion apparatus in accordance with claim 1, wherein the guide tube has a substantially rigid body and a pliable tip at a guide tube insertion end.

10. The insertion apparatus in accordance with claim 1, wherein the body and the guide tube both comprise a substantially rectangular cross-section.

11. An insertion apparatus for use with a rotary machine, the rotary machine defining an annular cavity extending along a circumference, said insertion apparatus comprising:
   an insertion end positionable within the annular cavity and configured to travel through the annular cavity;
   a steering end opposite said insertion end;
   a body extending from said insertion end to said steering end and sized to fit within the annular cavity, wherein said body has a first stiffness, wherein said body comprises a first continuous surface and a second continuous surface opposite the first continuous surface that curve along the circumference as said insertion end travels through the annular cavity;
   a stiffener integrally formed and fixed with respect to said body and extending from said steering end to said insertion end, wherein said stiffener has a second stiffness greater than the first stiffness and is configured to resist bending of said body;
   wherein the stiffener is fixed adjacent to one edge of the body;
   wherein the edge of the body corresponding to the location of the stiffener leads an opposite edge of the body that does not correspond to the stiffener during insertion into the annular cavity;
   wherein the stiffener is configured to resist bending and prevent the body from folding when being translated into the annular cavity;
   wherein the body and stiffener comprise a uniform and uninterrupted cross-section extending from the insertion end to the steering end;
   wherein (1) arrangement of the stiffener fixed and adjacent to one edge of the body and (2) integral formation of the body with the stiffener are cooperatively effective to provide the body with an overall stiffness, the overall stiffness being constant and unchanged prior to deformation of the body and after deformation of the body as the body curves along the circumference during insertion and movement of the body through the annular cavity;
   wherein the stiffener is uncontrolled during insertion and movement of the body through the annular cavity;
   at least one maintenance device coupled to said insertion end of said insertion apparatus;
   a displacement mechanism configured to adjust a position of said at least one maintenance device relative to said body; and
   a guide tube having a segmented body including segments that are positionable relative to each other, the body and stiffener axially movable through the segments of the guide tube,
   wherein the guide tube is curved to form an at least partially helical shape; and
   wherein said first continuous surface and said second continuous surface extend from said steering end to said insertion end, said body having a thickness defined between said first continuous surface and said second continuous surface less than about 0.02 inches, wherein the thickness is less than a width of said first continuous surface and said second continuous surface, the width extending in a direction transverse a longitudinal axis of the body such that the body is a ribbon-shaped body, and wherein said body is configured to curve in a direction perpendicular to said first continuous surface and said second continuous surface, wherein the stiffener has a stiffener thickness greater than the thickness of the body.

12. The insertion apparatus in accordance with claim 11, wherein the body and stiffener are axially movable through the segments of the guide tube.

13. The insertion apparatus in accordance with claim 12, wherein the guide tube has a substantially rigid body and a pliable tip at a guide tube insertion end.

14. A method of inspecting a rotary machine, the rotary machine defining an annular cavity extending along a circumference, said method comprising:
   positioning a guide tube in a port of the rotary machine to define a path for an insertion apparatus into the annular cavity, the guide tube having a substantially rigid body and a pliable tip at a guide tube insertion end, the insertion apparatus comprising:
   an insertion end positionable within the annular cavity and configured to travel through the annular cavity;
   a steering end opposite said insertion end;
   a body extending continuously from said insertion end to said steering end and sized to fit within the annular cavity, wherein said body is formed of a flexible material having a first stiffness and curves along the circumference as said insertion end travels through the annular cavity;
   a stiffener integrally formed and fixed with respect to said body and extending from said steering end to said insertion end, wherein said stiffener has a second stiffness that is greater than the first stiffness and is configured to resist bending of said body, wherein the guide tube is curved to form an at least partially helical shape;
   wherein the stiffener is fixed adjacent to one edge of the body;
   wherein the edge of the body corresponding to the location of the stiffener leads an opposite edge of the body that does not correspond to the stiffener during inertion into the annular cavity;

wherein the stiffener is configured to resist bending and prevent the body from folding when being translated into the annular cavity;

wherein the body and stiffener comprise a uniform and uninterrupted cross-section extending from the insertion end to the steering end;

at least one maintenance device coupled to said insertion end of said insertion apparatus; and a displacement mechanism configured to adjust a position of said at least one maintenance device relative to said body;

positioning the insertion apparatus along the path and into the annular cavity;

guiding the body of the insertion apparatus through the guide tube such that the substantially rigid body of the guide tube does not deform during guiding of the insertion apparatus therethrough and the pliable tip is deformable when contacted by the insertion apparatus;

directing the insertion end of the insertion apparatus through the annular cavity without controlling the stiffener; and positioning the at least one maintenance device adjacent a portion of the rotary machine using the displacement mechanism;

wherein (1) arrangement of the stiffener fixed and adjacent to one edge of the body and (2) the integral formation of the body with the stiffener are cooperatively effective to provide the body with an overall stiffness, the overall stiffness being constant and unchanged prior to deformation of the body and after deformation of the body as the body curves along the circumference during insertion and movement of the body through the annular cavity.

15. The method in accordance with claim 14, wherein said at least one maintenance device comprises at least one of the following: a mechanical sensor, a thermal sensor, a magnetic sensor, an acoustic sensor, and an electromagnetic sensor.

16. The method in accordance with claim 14, wherein said guide tube includes a plurality of positionable segments.

17. The method in accordance with claim 14, wherein said guide tube is coupled to the port and is sized and shaped to extend from the port to the annular cavity, said guide tube configured to guide said insertion apparatus through the port and into the annular cavity.

18. The method in accordance with claim 14, wherein positioning the at least one maintenance device adjacent a portion of the rotary machine using a displacement mechanism configured to adjust a position of the at least one maintenance device relative to the body comprises pivoting the at least one maintenance device about the insertion end of the insertion apparatus.

19. The method in accordance with claim 14, wherein positioning the at least one maintenance device adjacent a portion of the rotary machine using a displacement mechanism configured to adjust a position of the at least one maintenance device relative to the body comprises inflating a bladder coupled to the at least one maintenance device.

* * * * *

UNITED STATES PATENT AND TRADEMARK OFFICE
CERTIFICATE OF CORRECTION

| | | |
|---|---|---|
| PATENT NO. | : 12,405,187 B2 | Page 1 of 1 |
| APPLICATION NO. | : 16/696025 | |
| DATED | : September 2, 2025 | |
| INVENTOR(S) | : Deepak Trivedi et al. | |

It is certified that error appears in the above-identified patent and that said Letters Patent is hereby corrected as shown below:

In the Claims

In Column 13, Claim 14, Line 2, delete "inertion" and insert -- insertion --, therefor.

Signed and Sealed this
Twenty-fifth Day of November, 2025

John A. Squires
*Director of the United States Patent and Trademark Office*